(12) United States Patent
Burke et al.

(10) Patent No.: US 6,338,734 B1
(45) Date of Patent: Jan. 15, 2002

(54) METHOD AND APPARATUS FOR TROCHANTER FIXATION

(75) Inventors: Dennis W. Burke, Milton, MA (US); Ryan J. Schoenefeld, Fort Wayne, IN (US)

(73) Assignee: Biomet, Inc., Warsaw, IN (US)

( * ) Notice: Subject to any disclaimer, the term of this patent is extended or adjusted under 35 U.S.C. 154(b) by 0 days.

(21) Appl. No.: 09/525,549

(22) Filed: Mar. 14, 2000

(51) Int. Cl.$^7$ .............................................. A61B 17/56
(52) U.S. Cl. .......................................... 606/69; 606/74
(58) Field of Search .............................. 606/60, 69, 70, 606/71, 72, 74, 75

(56) References Cited

U.S. PATENT DOCUMENTS

| | | | |
|---|---|---|---|
| 3,824,995 A | * | 7/1974 | Getscher et al. |
| 4,146,022 A | | 3/1979 | Johnson et al. |
| 4,269,180 A | | 5/1981 | Dall et al. |
| 4,651,724 A | | 3/1987 | Berentey et al. |
| 4,988,350 A | | 1/1991 | Herzberg |
| 5,190,545 A | | 3/1993 | Corsi et al. |
| 5,197,989 A | | 3/1993 | Hinckfuss et al. |
| 5,356,410 A | | 10/1994 | Pennig |
| 5,462,547 A | | 10/1995 | Weigum |
| 5,741,259 A | | 4/1998 | Chan |
| 5,797,916 A | | 8/1998 | McDowell |

FOREIGN PATENT DOCUMENTS

FR 2712173 5/1995

\* cited by examiner

*Primary Examiner*—David O. Reip
(74) *Attorney, Agent, or Firm*—Harness, Dickey & Pierce, P.L.C.

(57) ABSTRACT

An implant for use in fixing an resected portion of a bone to a proximal portion of the bone. The implant includes an anatomically shaped plate member having a generally straight first portion and a second portion. The first portion has a bone receiving groove on its inner side and at least one lower wire receiving groove on its exterior side. The bone receiving groove is adapted to receive a generally straight portion of the proximal portion of the bone. The second portion is coupled to the first portion at a first end and terminates at a distal end in at least one inwardly directed hook-shaped member. The second portion is curved to generally match the contour of an end portion of the bone. The hook-shaped member is adapted to abut the resected portion of the bone to prevent the resected portion from migrating from the straight portion of the proximal portion of the bone. A method for fixing an resected greater trochanter to a proximal femur is also provided.

31 Claims, 1 Drawing Sheet

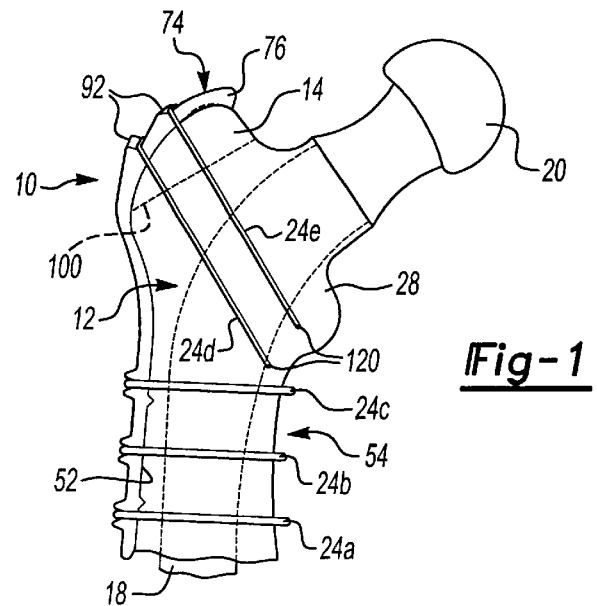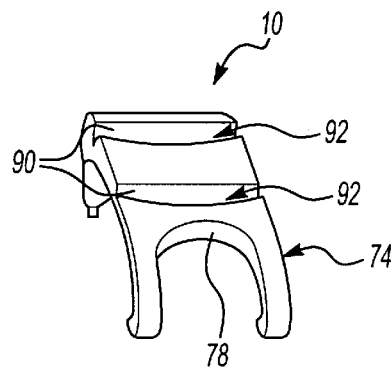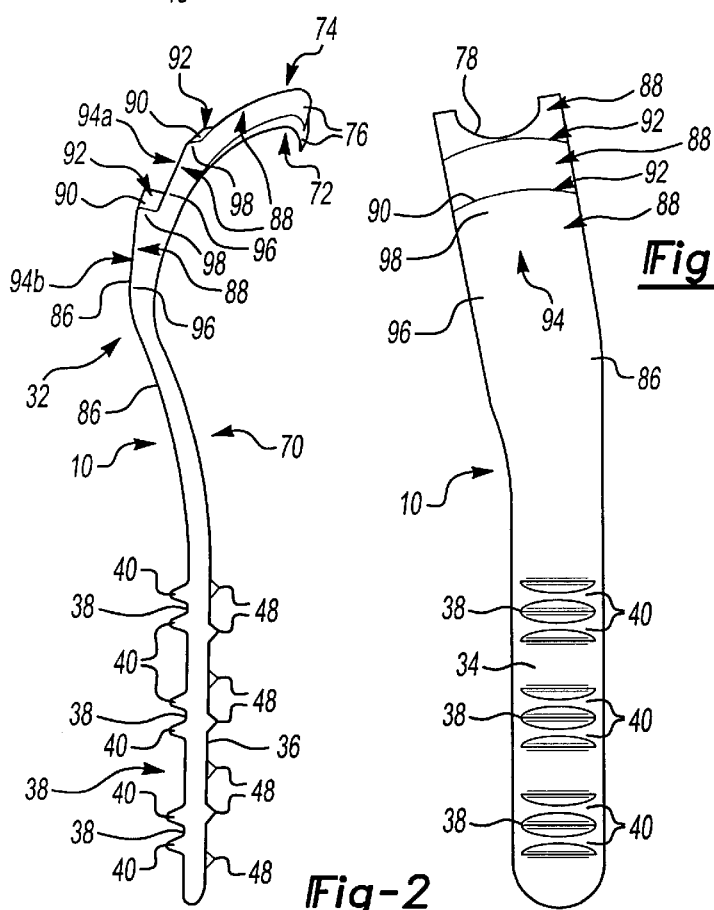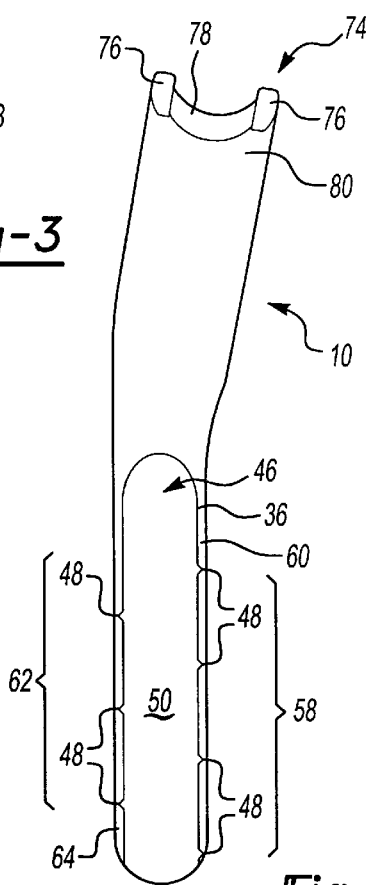

US 6,338,734 B1

METHOD AND APPARATUS FOR TROCHANTER FIXATION

TECHNICAL FIELD

The present invention relates generally to implants for use in bone surgery and more particularly to a method and apparatus for trochanter fixation.

BACKGROUND OF THE INVENTION

BACKGROUND ART

In many reconstructive procedures of the hip, the greater trochanter with its attached abductor musculature is often resected from the proximal femur and then retracted to permit the physician to approach the joint. After the femoral head is replaced with a prosthetic femoral component, the greater trochanter is relocated and fastened in place. Sound reattachment of the greater trochanter to the main shaft of the femur is necessary for the hip operation to provide good functional results. In this regard, sound reattachment of the greater trochanter requires that the greater trochanter be immobilized relative to the proximal femur until the bone has had time to fully heal.

Existing methods for reattachment of the greater trochanter include the use of U-bolts, bolts and clamps, and plates and screws. Perhaps the most common prior art method is to wire the greater trochanter in position using various techniques, such as a rigid H-shaped implant disclosed in U.S. Pat. No. 4,269,180 to Dall et al. These methods, however, have several drawbacks.

These drawbacks are primarily associated with the shape of the implant and the manner in which the forces exerted by the wires are directed into the femur. Many of the available implants lack an anatomical shape that conforms to the natural shape of the femur, rendering it more difficult to properly locate the implant and attach the wires in a manner that directs a clamping force into the femur in an optimal manner. In use, the abductor muscle applies a substantial force to the implant and wires, sometimes causing the greater trochanter to migrate relative to the proximal femur or the wires to be pulled through the bone against which it bears. In either event, proper fixation of the greater trochanter to the proximal femur is not obtained.

SUMMARY OF THE INVENTION

It is one object of the present invention to provide an anatomical implant for the reattachment of a resected portion of a bone to a proximal portion of a bone.

It is another object of the present invention to provide an anatomical implant for the reattachment of a resected greater trochanter to a proximal femur.

It is a further object of the present invention to provide an implant for the reattachment of a resected greater trochanter that positions a plurality of attachment wires so as to direct a clamping force into the femur in an improved manner.

It is yet another object of the present invention to provide a method for fixing a resected greater trochanter to a proximal femur.

In one form, the present invention provides an implant for use in fixing a resected portion of a bone to a proximal portion of the bone. The implant includes an anatomically shaped plate member having a generally straight first portion and a second portion. The first portion has an anatomically shaped bone receiving groove on its inner side and at least one lower wire receiving groove on its exterior side. The bone receiving groove is adapted to receive a generally straight portion of the proximal portion of the bone. The second portion is coupled to the first portion at a first end and terminates at a distal end in at least one inwardly directed hook-shaped member. The second portion is anatomically shaped to generally match the contour of an end portion of the bone. The hook-shaped member includes at least one tine that is adapted to abut the resected portion of the bone to prevent the resected portion from migrating from the straight portion of the proximal portion of the bone. A method for fixing a resected greater trochanter to a proximal femur is also provided.

BRIEF DESCRIPTION OF THE DRAWINGS

Additional advantages and features of the present invention will become apparent from the subsequent description and the appended claims, taken in conjunction with the accompanying drawings, wherein:

FIG. 1 is a partial view of a femur after an operation illustrating the use of an implant constructed in accordance with the teachings of a preferred embodiment of the present invention;

FIG. 2 is a right side view of the implant of FIG. 1;

FIG. 3 is a rear view of the implant of FIG. 1;

FIG. 4 is a front view of the implant of FIG. 1; and

FIG. 5 is an end view of the implant of FIG. 1.

DETAILED DESCRIPTION OF THE PREFERRED EMBODIMENT

With reference to FIG. 1, an implant constructed in accordance with the teachings of the preferred embodiment of the present invention is generally indicated by reference numeral 10. The implant 10 is illustrated in operative association with a femur 12. In a hip joint replacement operation, the greater trochanter 14 is severed from the remainder of the femur 12 and the femoral head is removed. Removal of the greater trochanter 14 enables the muscle secured thereto to be folded back to permit greater exposure of and access to the site of the operation. The medullary cavity of the femur 12 is then reamed and prepared to receive the stem 18 of a prosthetic head 20 which replaces the femoral head. The implant 10 is anatomically shaped to correspond to the shape of the femur 12. The implant 10 is secured to the femur 12 via a plurality of attachment wires 24 to prevent the greater trochanter 14 from migrating relative to the proximal portion 28 of the femur 12. The wires 24 may be, for example, a mono-strand wire or a braided cable.

With additional reference to FIGS. 2 through 5, the implant 10 is shown to include a generally straight first portion 30 and a curved second portion 32. The implant 10 is formed from a suitable material, such as stainless steel, titanium or cobalt chrome. However, it is presently preferred that the implant 10 be formed from cobalt chrome, as this material is well suited for use in a casting process to form the implant 10.

The first portion 30 of the implant 10 includes an outer side 34 and an inner side 36. The outer side 34 includes a plurality of first wire retention grooves 38 for receiving wires 24*a*, 24*b* and 24*c*. In the particular embodiment illustrated, each of the wire retention grooves 38 is formed by a pair of raised protrusions 40.

The inner side 36 of the first portion 30 includes a bone receiving groove 46 and a plurality of spikes 48. The bone receiving groove 46 has an anatomically-shaped arcuate surface 50 that is contoured to match the surface 52 of a straight portion 54 of the proximal femur 28. The anatomically-shaped arcuate surface 50 of the bone receiving groove 46 permits the first portion 30 to abut against the straight portion 54 of the proximal femur 28 in a manner which aids in the positioning of the implant 10 relative to the femur 12.

Each of the spikes 48 is coupled to and extends in a direction normal to the inner side 36 of the first portion 30. A first portion 58 of the spikes is positioned on a first edge 60 of the inner side 36 and a second portion 62 of the spikes is positioned on a second side 64 of the inner side 36. The spikes 48 forming the first portion of spikes 58 are spaced apart in an axial direction along the length of first portion 30. The spikes 48 forming the second portion of spikes 62 are also spaced apart in an axial direction along the length of first portion 30, but the each spike 48 of the second portion of spikes 62 is positioned axially between two of the spikes 48 of the first portion of spikes 58. The first and second portions of spikes 58 and 62 cooperate to prevent the first portion 30 from moving axially or radially relative to the proximal femur 28.

The second portion 32 of the implant 10 includes a first end 70 which is coupled to the first portion 30 of the implant 10 and a proximal end 72 which terminates at a hook-shaped member 74. In the particular embodiment illustrated, the implant 10 is angled rearwardly and curves inwardly from the first end 70 to the distal end 72 and as such, the implant 10 is configured as for use on a right femur 12. Those skilled in the art should readily understand that an implant for a left femur may be constructed by mirroring the features of the second portion 32 about a longitudinal axis of the first portion 30.

The hook-shaped member 74 includes at least one tine 76 that is adapted to abut the resected greater trochanter 14 to prevent the resected greater trochanter 14 from migrating from the proximal femur 28. In the particular embodiment illustrated, a U-shaped aperture 78 is formed in the hook-shaped member 74 to eliminate interference between the inner surface 80 of the hook-shaped member 74 and the greater trochanter 14. Construction of implant 10 in this manner is advantageous in that it permits the overall size of the implant 10 to be reduced.

The outer surface 86 of the second portion 32 includes a plurality of ramp members 88 and ledge members 90. A plurality of second wire grooves 92 are formed by the intersection of the ramp members 88 and the ledge members 90. Each of the ramp members 88 is adapted to guide a wire 24 into a second wire groove 92 when tension is applied to the wire 24. In the example provided, the ramp members 88 are formed by the hook-shaped member 74 and by a plurality of ramp-shaped protrusions 94. Each of the ramp-shaped protrusions 94 has a tip portion 96 and an end portion 98, with the ramp-shaped protrusion 94 tapering outwardly from the tip portion 96 to the end portion 98. In the example provided, the ledge members 90 are formed by the end portions 98 of each of the ramp-shaped protrusions 94. The ramp-shaped protrusions 94 are positioned on the outer surface 86 of the second portion 32 such that the tip portion 96 of a first one of the ramp-shaped protrusions 94a abuts the end portion 98 of a second one of the ramp-shaped protrusions 94b.

The anatomically-shaped second portion 32 of the implant 10 aids in the positioning of the implant 10 and permits the second wire grooves 92 to be oriented in a manner such that the clamping force produced by the wires 24 is directed in a predetermined manner. For example, the second wire grooves 92 may be positioned along the outer surface 86 of the second portion 32 such that the clamping force produced by the wires 24 is oriented in a direction that is normal to the plane at which the greater trochanter 14 was severed.

Returning to FIG. 1, a method for securing a resected greater trochanter 14 to a proximal femur 28 will be discussed in detail. The method begins by providing an anatomically-shaped implant, such as the implant 10. The implant 10 is next placed against the resected greater trochanter 14 and the proximal femur 28 such that the arcuate surface 50 of the bone receiving groove 46 abuts a generally straight portion 54 of the proximal femur 28 and the tines 76 of the hook-shaped member 74 abut the resected greater trochanter 14. Advantageously, the anatomical shape of the implant 10 aids in the accurate placement of it relative to the femur 12.

A plurality of wires are next secured around the implant 10. The wires 24 may be secured via a coupler such as a cable sleeve or they may be inserted through holes 120 that have been drilled in the proximal femur 28. The wires 24 are then tensioned to urge the first portion 30 of the implant against the straight portion 54 of the proximal femur 28 and the second portion 32 of the implant 10 against the resected greater trochanter 14. Tensioning of wires 24d and 24e permits the tines 76 of the hook-shaped member 74 to embed into the resected greater trochanter 14 to prevent the resected greater trochanter 14 from migrating relative to the proximal femur 28.

While the invention has been described in the specification and illustrated in the drawings with reference to a preferred embodiment, it will be understood by those skilled in the art that various changes may be made and equivalents may be substituted for elements thereof without departing from the scope of the invention as defined in the claims. In addition, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the foregoing description and the appended claims.

What is claimed is:

1. An implant for use in fixing a resected portion of a bone to a proximal portion of the bone, the bone having a generally straight portion and a contoured end portion, the implant comprising:

an anatomically shaped plate member having a generally straight first portion and a second portion;

the first portion of the plate member having an inner side and an outer side, the inner side of the first portion including an anatomically-shaped bone receiving groove adapted to receive a generally straight portion of the bone, the outer side of the first portion including a first wire receiving groove adapted to receive a wire to secure the first portion of the plate member to the straight portion of the bone;

the second portion of the plate member extending from the first portion and terminating at its proximal end in at least one inwardly directed hook-shaped member, the second portion being anatomically-shaped to generally match the contour of an end portion of the bone;

the hook-shaped member including at least one tine that is adapted to abut the resected portion of the bone to prevent the resected portion from migrating relative to the proximal portion of the bone.

2. The implant of claim 1, wherein the second portion of the implant is formed in a direction that is specific to a lateral side of a patient.

3. The implant of claim 1, wherein the second portion further includes a second wire receiving groove adapted to receive and orient a wire in a manner that applies a clamping force in a predetermined direction to inhibit relative motion between the resected portion of the bone and the proximal portion of the bone.

4. The implant of claim 3, wherein the second portion further includes a ramp member and a ledge member, the ramp member having a tip portion, the second wire receiving groove being formed at a location where the tip portion of the ramp member abuts the ledge member.

5. The implant of claim 4, wherein the ramp member is adapted to guide a wire into the second wire groove when tension is applied to the wire.

6. The implant of claim 5, wherein the ramp member tapers inwardly toward the tip portion.

7. The implant of claim 5, wherein the ramp member curves inwardly toward the tip portion.

8. The implant of claim 1, wherein the first portion further includes a plurality of spikes coupled to the inner side of the first portion, the plurality of spikes adapted to engage the straight portion of the bone to prevent the first portion from moving relative to the proximal portion of the bone.

9. The implant of claim 8, wherein the plurality of spikes are formed along the edges of the inner side of the first portion of the plate member.

10. The implant of claim 9, wherein a first portion of the plurality of spikes and a second portion of the plurality of spikes are coupled to first and second edges on the inner side of the first portion of the plate member, respectively, the first portion of spikes being spaced apart along a first axis, each of the second portion of spikes being positioned along a second axis parallel the first axis and between a pair of adjacent spikes in the first portion of spikes.

11. The implant of claim 1, wherein a U-shaped aperture is formed in the hook-shaped member, the U-shaped aperture adapted to prevent interference between an inner surface of the implant and a greater trochanter.

12. An implant for use in fixing a resected portion of the greater trochanter to a proximal femur, the proximal femur having a straight portion and a contoured end portion, the implant comprising an anatomically shaped plate member having a generally straight first portion and a second portion, the first portion of the plate member having an inner side adapted to abut a generally straight portion of the proximal femur, the second portion of the plate member extending from the first portion and terminating at the proximal end in at least one inwardly directed hook-shaped member, the second portion being skewed to the first portion and anatomically-shaped to generally match the contour of an end portion of a femur, the hook-shaped member including at least one tine that is adapted to abut the resected portion of the greater trochanter to prevent the resected portion of the greater trochanter from migrating relative to the proximal femur.

13. The implant of claim 12, wherein the second portion of the implant is formed in a direction that is specific to a lateral side of a patient.

14. The implant of claim 12, wherein a U-shaped aperture is formed in the hook-shaped member, the U-shaped aperture adapted to prevent interference between an inner surface of the implant and the greater trochanter.

15. An implant for use in fixing a resected portion of the greater trochanter to a proximal femur, the proximal femur having a straight portion and a contoured end portion, the implant comprising an anatomically shaped plate member having a generally straight first portion and a second portion, the first portion of the plate member having an inner side adapted to abut a generally straight portion of the proximal femur, the second portion of the plate member extending from the first portion and terminating at the proximal end in at least one inwardly directed hook-shaped member, the second portion being anatomically-shaped to generally match the contour of an end portion of a femur, the hook-shaped member including at least one tine that is adapted to abut the resected portion of the greater trochanter to prevent the resected portion of the greater trochanter from migrating relative to the proximal femur, the second portion further including a wire receiving groove adapted to receive and orient a wire in a manner that applies a clamping force in a predetermined direction to inhibit relative motion between the resected greater trochanter and the proximal femur.

16. An implant for use in fixing a resected portion of the greater trochanter to a proximal femur, the proximal femur having a straight portion and a contoured end portion, the implant comprising an anatomically shaped plate member having a generally straight first portion and a second portion, the first portion of the plate member having an inner side adapted to abut a generally straight portion of the proximal femur, the second portion of the plate member extending from the first portion and terminating at the proximal end in at least one inwardly directed hook-shaped member, the second portion being anatomically-shaped to generally match the contour of an end portion of a femur, the hook-shaped member including at least one tine that is adapted to abut the resected portion of the greater trochanter to prevent the resected portion of the greater trochanter from migrating relative to the proximal femur, the second portion further including a ramp member and a ledge member, the ramp member having a tip portion, the wire receiving groove being formed at a location where the tip portion of the ramp member abuts the ledge member.

17. The implant of claim 14, wherein the ramp member is adapted to guide a wire into the wire groove when tension is applied to the wire.

18. The implant of claim 17, wherein the ramp member tapers inwardly toward the tip portion.

19. The implant of claim 17, wherein the ramp member curves inwardly toward the tip portion.

20. An implant for use in fixing a resected portion of the greater trochanter to a proximal femur, the proximal femur having a straight portion and a contoured end portion, the implant comprising an anatomically shaped plate member having a generally straight first portion and a second portion, the first portion of the plate member having an inner side adapted to abut a generally straight portion of the proximal femur, the first portion further including a plurality of spikes coupled to the inner side of the first portion, the plurality of spikes adapted to engage the straight portion of the proximal femur to prevent the first portion from moving relative to the proximal femur, the second portion of the plate member extending from the first portion and terminating at the proximal end in at least one inwardly directed hook-shaped member, the second portion being anatomically-shaped to generally match the contour of an end portion of a femur, the hook-shaped member including at least one tine that is adapted to abut the resected portion of the greater trochanter to prevent the resected portion of the greater trochanter from migrating relative to the proximal femur.

21. The implant of claim 20, wherein the plurality of spikes are formed along the edges of the inner side of the first portion.

22. The implant of claim 20, wherein a first portion of the plurality of spikes and a second portion of the plurality of spikes are coupled to first and second edges on the inner side of the first portion of the plate member, respectively, the first portion of spikes being spaced apart along a first axis, each of the second portion of spikes being positioned along a second axis parallel the first axis and between a pair of adjacent spikes in the first portion of spikes.

23. An implant for use in fixing a resected portion of the greater trochanter to a proximal femur, the proximal femur having a straight portion and a contoured end portion, the implant comprising an anatomically shaped plate member having a generally straight first portion and a second portion, the first portion of the plate member having an inner side adapted to abut a generally straight portion of the proximal femur, the first portion of the plate member also including an outer side having at least one wire receiving groove adapted to receive a wire to secure the first portion of the plate member to the straight portion of the proximal femur, the second portion of the plate member extending from the first portion and terminating at the proximal end in at least one inwardly directed hook-shaped member, the second portion being anatomicallyshaped to generally match the contour of an end portion of a femur, the hook-shaped member including at least one tine that is adapted to abut the resected portion of the greater trochanter to prevent the resected portion of the greater trochanter from migrating relative to the proximal femur.

24. An implant for use in fixing a resected portion of the greater trochanter to a proximal femur, the implant comprising an anatomically shaped plate member having an inner surface and an outer surface, the inner surface generally conforming to a profile of a femur, the outer surface having a ledge member and a ramp member, the ramp member abutting the ledge member and forming a wire groove therebetween, the ramp member adapted to guide a wire into the wire groove when tension is applied to the wire.

25. The implant of claim 24, wherein at least a portion of the plate member is formed in a direction that is specific to a lateral side of a patient.

26. A method for securing a resected portion of the greater trochanter to a proximal femur comprising the steps of:
providing an anatomically-shaped implant having a plate member with a generally straight first portion and a second portion, the first portion having an inner surface with an anatomically-shaped bone receiving groove, the second portion being anatomically-shaped to generally match the contour of the greater trochanter, the second portion extending from the first portion and terminating at the proximal end at an inwardly directed hook-shaped member, the hook-shaped member terminating in at least one tine;
placing the implant against the resected portion of the greater trochanter and the proximal femur such that the bone receiving groove in the first portion of the plate member abuts a generally straight portion of the proximal femur and the at least one tine of the hook-shaped member abuts the resected portion of the greater trochanter;
securing a wire around the implant; and
tensioning the wire to urge the second portion of the implant against the resected portion of the greater trochanter such that the at least one tine of the hook-shaped member embeds into the resected portion of the greater trochanter to prevent the resected portion of the greater trochanter from migrating relative to the proximal femur.

27. The method of claim 26, wherein the step of securing the wire around the implant includes the steps of:
drilling a hole in the proximal femur;
inserting the wire through the hole; and
wrapping the wire around the second portion of the implant.

28. The method of claim 26, further comprising the steps of:
securing a second wire around the implant; and
tensioning the second wire to urge the first portion of the implant against the generally straight portion of the proximal femur.

29. A method for securing a resected portion of the greater trochanter to a proximal femur comprising the steps of:
providing an anatomically-shaped implant having a plate member with a generally straight first portion and a second portion, the first portion having an anatomically-shaped bone receiving groove on its inner side, the second portion being anatomically-shaped to generally match the contour of the greater trochanter, the second portion extending from the first portion, the second portion including a ledge member and a ramp member, the ramp member abutting the ledge member and forming a wire groove therebetween;
placing the implant against the resected portion of the greater trochanter and the proximal femur such that the bone receiving groove in the first portion of the plate member abuts a generally straight portion of the proximal femur and the second portion of the plate member abuts the resected portion of the greater trochanter;
securing a wire around the implant; and
tensioning the wire against the ramp member, whereby the ramp member guides the wire into the wire groove and urges the second portion of the implant against the resected greater trochanter.

30. The method of claim 29, wherein the step of securing the wire around the implant includes the steps of:
drilling a hole in the proximal femur;
inserting the wire through the hole; and
wrapping the wire around the implant.

31. An implant for use in fixing an resected portion of the greater trochanter to a proximal femur, the proximal femur having a straight portion and a contoured end portion, the implant comprising an anatomically shaped plate member having a generally straight first portion and a second portion, the first portion of the plate member having an inner side adapted to abut a generally straight portion of the proximal femur, the second portion of the plate member extending from the first portion, the second portion being skewed to the first portion and anatomically-shaped to generally match the contour of an end portion of a femur.

* * * * *

UNITED STATES PATENT AND TRADEMARK OFFICE
CERTIFICATE OF CORRECTION

PATENT NO. : 6,338,734 B1 Page 1 of 1
DATED : January 15, 2002
INVENTOR(S) : Dennis W. Burke and Ryan J. Schoenefeld It is certified that error appears in the above-identified patent and that said Letters Patent is hereby corrected as shown below:

Title page,
Item [57], ABSTRACT,
Line 2, "an" should be -- a --.
Line 17, "an" should be -- a --.

Column 6,
Line 41, "claim 14" should be -- claim 16 --.

Column 7,
Line 27, "anatomicallyshaped" should be -- anatomically-shaped --.

Column 8,
Line 51, "an" should be -- a --.

Signed and Sealed this

Eighth Day of October, 2002

*Attest:*

*Attesting Officer*

JAMES E. ROGAN
*Director of the United States Patent and Trademark Office*